United States Patent [19]

Reedy et al.

[11] Patent Number: 4,556,726

[45] Date of Patent: Dec. 3, 1985

[54] PROCESS FOR CONVERTING OCTAMETHYLCYCLOTETRASILOXANE TO DECAMETHYLCYCLOPENTASILOXANE

[75] Inventors: James D. Reedy; John J. Walsh, both of Marietta, Ohio

[73] Assignee: Union Carbide Corporation, Danbury, Conn.

[21] Appl. No.: 689,991

[22] Filed: Jan. 9, 1985

[51] Int. Cl.$^4$ ............................................. C07F 7/08
[52] U.S. Cl. ................................................... 556/460
[58] Field of Search ......................................... 556/460

[56] References Cited

U.S. PATENT DOCUMENTS

| | | | |
|---|---|---|---|
| 2,618,648 | 11/1952 | Bluestein | 556/460 |
| 2,769,829 | 11/1956 | Dobay | 556/460 |
| 3,021,297 | 2/1962 | George | 556/460 X |
| 4,423,240 | 12/1983 | Yeboah | 556/460 |

*Primary Examiner*—Paul F. Shaver
*Attorney, Agent, or Firm*—Paul W. Leuzzi, II

[57] ABSTRACT

Method for producing decamethylcyclopentasiloxane (cyclic pentamer) from octamethylcyclotetrasiloxane (cyclic tetramer) by heating said cyclic tetramer in the presence of an aqueous hydrochloric acid solution and a salt of a protonated amine having at least one nitrogen-bonded monovalent hydrocarbon group having 5 to 14 carbon atoms.

14 Claims, No Drawings

PROCESS FOR CONVERTING OCTAMETHYLCYCLOTETRASILOXANE TO DECAMETHYLCYCLOPENTASILOXANE

BACKGROUND OF THE INVENTION

1. Field of the Invention

This invention relates to the production of decamethylcyclopentasiloxane, hereinafter referred to as "the cyclic pentamer", from octamethylcyclotetrasiloxane, hereinafter referred to as "the cyclic tetramer".

2. Prior Art

Decamethylcyclopentasiloxane has been found to be increasingly useful in cosmetic formulations including anti-perspirant formulations. As a consequence, efforts in the trade are being directed towards increasing the volume of production of the cyclic pentamer.

U.S. Pat. No. 4,412,081 seeks to produce the cyclic pentamer from the cyclic tetramer by heating the cyclic tetramer in the presence of a normal $C_{6-16}$ alkyl sulfonic acid and aqueous hydrogen chloride at a temperature in excess of 50° C. but fails to disclose the production of the cyclic pentamer by contacting the cyclic tetramer with aqueous hydrochloric acid and a protonated amine.

U.S. Pat. No. 3,983,148 discloses a process for producing a mixture of cyclic siloxanes by hydrolyzing and condensing a hydrolyzable organo silicon compound such as dichlorodimethylsilane in the presence of aqueous hydrochloric acid and a cationic surface active agent which can be formed in situ by adding an amine, carboxylic acid, alcohol, nitrile, mercaptan, phosphine or quaternary phosphonium salt to the aqueous hydrochloric acid. There is however no disclosure or suggestion of contacting the cyclic tetramer with aqueous hydrochloric acid and a protonated amine for the purpose of converting the cyclic tetramer to the cyclic pentamer.

U.S. Pat. No. 4,447,630 discloses a method for making a mixture of cyclopolysiloxanes by hydrolyzing and condensing diorganodichlorosilanes and aqueous hydrochloric acid in the presence of a perfluorinated alkyl sulfonic acid salt but fails to disclose, teach or suggest the production of the cyclic pentamer from the cyclic tetramer by contacting the latter with aqueous hydrochloric acid and a protonated amine.

U.S. Pat. No. 4,222,952 discloses the equilibration of organosiloxanes and other rearrangements of siloxane bonds by contacting the organosiloxane with a solid perfluorinated polymer containing pendant sulfonic acid groups but fails to disclose, teach or suggest the conversion of the cyclic tetramer to the cyclic pentamer by contacting the cyclic tetramer with aqueous hydrochloric acid and a protonated amine.

SUMMARY OF THE INVENTION

The present invention is based upon the unexpected discovery that cyclic tetramer ($D_4$) can be converted to the cyclic pentamer ($D_5$) by heating the tetramer in the presence of an aqueous hydrochloric acid solution and a salt of a protonated amine having a monovalent hydrocarbon group containing 5 to 14 carbon atoms bonded to the nitrogen of the amine and provides high yields of the cyclic pentamer within a reasonable period of time, e.g., as short as 15 minutes or less.

The salt of the protonated amine can be formed in situ by adding a suitable amine to the aqueous hydrochloric acid solution. Suitable amines for this purpose include primary, secondary and tertiary amines having at least one nitrogen-bonded monovalent hydrocarbon group containing from 5 to 14 carbon atoms and can be represented by the formula NRR'R'' wherein R is a monovalent hydrocarbon group, preferably an alkyl group, having 5 to 14 carbon atoms and each of R' and R'' is a hydrogen atom or a monovalent hydrocarbon group, preferably an alkyl group, having 1 to 4 carbon atoms. Suitable amines for use in this invention specifically include n-octylamine, 2-ethylhexylamine, n-pentylamine, n-hexylamine, n-cetyldimethylamine, n-dodecylamine, n-dodecyldipropylamine, n-octylmethylamine, n-nonylamine, n-tetradecylamine and the like.

In addition, the salt of the protonated amine can be added as such to the aqueous hydrochloric acid pursuant to this invention. Suitable protonated amine salts include those having the formula: $RR'R''N^+H.X^-$ wherein R, R' and R'' are as previously defined and X is a halogen ion or the anion of a strong mineral acid such as HCl, $H_2SO_4$, $H_3PO_4$. For example, X can be $Cl^-$, $I^-$, $Br^-$, $SO_4^=$ and the like. The amount of amine or protonated amine utilized in the process of this invention can range from 0.1 to 10 wt. %, preferably 0.5 to 5 wt. %, based on the amine (not protonated) and the total weight of the reaction mixture, i.e., the total weight of aqueous hydrochloric acid solution, cyclic tetramer ($D_4$), and the amine (not protonated).

The temperature under which the reaction pursuant to this invention is carried out can range over a wide range in excess of 60° C. More specifically, the reaction will proceed slowly below 60° C. but the reaction is so slow as to be of very limited use commercially. Temperatures as high as 180° C. and above can also be employed but there is a risk of forming undesirable amounts of trifunctional siloxy units, $MeSiO_{1.5}$.

The pressure used in carrying out the reaction also is not narrowly critical since the reaction of the process of this invention is in the condensed phase. Pressure however does indirectly impact on the reaction rate because of its influence on the amount of hydrogen chloride dissolved in the water in the aqueous hydrochloric acid solution. In general, more hydrogen chloride is dissolved in the water at higher pressures thus providing a more highly concentrated aqueous hydrochloric acid solution and therefore a faster rate of conversion of $D_4$ to $D_5$. However, based on practical process considerations, the range of pressures useable in the process of this invention extends from 1 to 50 atmospheres, preferably 1 to 10 atmospheres.

In addition to the conversion rate from $D_4$ to $D_5$ being influenced by the concentration of amine or protonated amine salt, temperature and pressure, it is influenced by the hydrochloric acid concentration and the mixing intensity. The conversion rate from $D_4$ to $D_5$ is proportional to the rate of agitation. Because the reaction or conversion is interfacial, moderate to high mixing intensities are preferred and in general mixing rates of 500 to 850 rpm provide good results. It is understood however that the mixing efficiency or intensity is also affected by factors other than the speed of rotation, for example, the number and design of the mixing blades will affect the mixing intensity and the rpm speed for providing a desirable mixing intensity.

The concentration of hydrogen chloride in water in the aqueous hydrochloric acid solution also affects the conversion rate, the conversion rate being enhanced by a higher ratio of hydrogen chloride to water in the aqueous hydrochloric acid solution; that is, the more concentrated aqueous hydrochloric acid solutions provide improved conversion rates. The conversion rate also can be increased by increasing the ratio of the aqueous hydrochloric acid solution to the $D_4$ being converted. Preferably the ratio of hydrogen chloride to water is at least 0.25 or greater. More specifically, 36 wt. % aqueous hydrochloric acid solutions are preferred and 20 wt. % aqueous hydrochloric acid solutions provide acceptable results.

The preferred ratio of $D_4$ to aqueous hydrochloric acid solution is less than 9, preferably, for example, 0.3 to 5. It is desirable to conduct the reaction or conversion in the shortest possible reaction time so as to minimize the formation of siloxane polymers which would represent a loss in the conversion of $D_4$ to $D_5$. Optimum process conditions will vary depending upon the desired conversion rate and the precise level or condition of each of the process variables outlined hereinabove.

After the desired conversion rate has been reached, the reaction mixture is allowed to stand for a sufficient period of time to effect a phase separation of a siloxane product phase and an aqueous phase. The siloxane product phase is then neutralized in any suitable manner, such as by washing with water one or more times and/or by treatment with an alkaline reagent such as sodium bicarbonate. After neutralization and washing, the siloxane product can be filtered to further remove foreign particulate material. After filtration, the product can then be fractionated if desired to separate the cyclic polymers from the linear polymers. The cyclic polymers can be fractionated by distillation, for example, to separate the cyclic pentamer from the cyclic tetramer and hexamer and other cyclic polymers.

A particularly useful feature of the present invention is that it can be integrated with systems currently in use for hydrolyzing and condensing dimethyldichlorosilane to provide increased amounts of cyclic pentamer ($D_5$). For example, the well known process for hydrolyzing dimethyldichlorosilane, e.g., as described in U.S. Pat. No. 3,983,148, contacts the dimethyldichlorosilane with a protonated amine salt, e.g. n-octylamine hydrochloride and an aqueous hydrochloric acid solution to produce "acid cyclic" hydrolyzates which then are neutralized and/or water washed to provide a mixture of linear polysiloxanes and cyclic polysiloxanes. The linear products can be separated from the cyclic products by any convenient means, e.g. fractionation, and the cyclic tetramer, pentamer, hexamer and heptamer can be each separated from the other by fractional distillation for example.

The cyclic tetramer thus recovered can be treated pursuant to this invention, that is, by first mixing it with an amine or protonated amine salt and an aqueous hydrochloric acid solution. The resulting mixture pursuant to this invention is allowed to phase separate. The aqueous phase containing aqueous hydrochloric acid and amine protonate salt are then separated and recycled for contact with fresh cyclic tetramer ($D_4$) produced by fractionation of the mixture of linear and cyclic polysiloxanes produced by the hydrolysis of dimethyldichlorosilane. The polysiloxane phase containing the increased amounts of $D_5$ converted from $D_4$ are then fed to the "acid cyclic" hydrolyzate as mentioned above prior to neutralization and water wash of the hydrolyzate. The $D_5$ converted from the $D_4$ is then neutralized and washed with water with the hydrolyzate and later recovered in the subsequent fractionation of the cyclic portion of the neutralized and water washed hydrolyzate.

The following examples are presented. In the examples all percentages and all ppm figures are on a weight basis unless otherwise indicated and all temperatures are on the Centigrade scale. In addition, the following abbreviations are used.

| | |
|---|---|
| rpm | revolutions per minute |
| ppm | parts per million |
| Me | methyl |
| ml | milliliter |
| HCl | hydrochloric acid |
| Conc. HCl | concentrated HCL, i.e. a solution containing 36 wt. % HCl and 64 wt. % water |
| Tr | trace amounts |
| $D_3$ | dimethylsiloxane cyclic trimer $[Me_2SiO]_3$ |
| $D_4$ | dimethylsiloxane cyclic tetramer $[Me_2SiO]_4$ |
| $D_5$ | dimethylsiloxane cyclic pentamer $[Me_2SiO]_5$ |
| $D_6$ | dimethylsiloxane cyclic hexamer $[Me_2SiO]_6$ |
| $D_7$ | dimethylsiloxane cyclic heptamer $[Me_2SiO]_7$ |
| $D_8$ | dimethylsiloxane cyclic octamer $[Me_2SiO]_8$ |
| $D_9$ | dimethylsiloxane cyclic nonamer $[Me_2SiO]_9$ |
| $D_{10}$ | dimethylsiloxane cyclic decamer $[Me_2SiO]_{10}$ |

EXAMPLE 1

Into a 1000 ml bottom takeoff pot equipped with a mechanical agitator, heating mantel provided with a pot watcher, (Therm-O-Watch), a Friedrich water condenser, a thermometer, and charge funnel, there were charged 383.81 grams of concentrated HCl. Thereafter, agitation of the pot contents was begun using moderate speed and 5.84 grams of n-octylamine were charged to the pot through the funnel. Thus, the initial charge contained 98.5% concentrated HCl and 1.5% n-octylamine. Upon addition of the n-octylamine, heavy fumes were noted in the pot and solids formation was noted on the inner end of the charged funnel. The pot was then heated to 65° C. over a period of about 17 minutes at which time fumes were noted coming through the condenser. Heating was continued for another 20 minutes during which time the temperature reached 90° C., which temperature was held by the pot watcher. Thereafter, the addition of $D_4$ was begun and continued until about half of the $D_4$ was added. The $D_4$ used contained 99.4% $D_4$, 212 ppm $D_3$, 5106 ppm $D_5$, 102 ppm $D_6$, 42 ppm $D_7$, 34 ppm $D_8$ and 14 ppm $D_9$. The total charge of $D_4$ to be added was 584.54 grams. The temperature at this point was about 83° C. and timing was begun at this point, i.e. time zero was recorded when approximately one-half the $D_4$ charge had been added. The remaining half of the $D_4$ charge was added within a 5 minute period at which time the pot temperature was 80° C. At this point the materials charged to the pot amounted to contained 60% $D_4$, 39.4% concentrated HCl and 0.6% n-octylamine on a non-protonated basis. The temperature of the pot contents was lined out at 90° C. At 15 minutes from time zero a 78.7 gram sample was removed using the bottom takeoff. It contained an extreme haze and was allowed to phase separate (for about 2 minutes). The top layer that formed was decanted, neutralized with sodium bicarbonate and filtered. The filtered sample then was analyzed by vapor phase chromatography and was found to have the amounts and types of cyclic polymers designated in Table 1. At each of the times from time zero designated in Table 1, a sample of approximately 71 through 77 grams was taken through the bottom takeoff, phase separated, and the top layer that formed was decanted, neutralized and filtered. The vapor phase chromatography (VPC) analysis for each of the samples are provided in Table 1.

TABLE 1

| Sample Number | Time From Time Zero | Sample Weight (Grams) | Chromatography Analysis (VPC), % | | | | | | |
|---|---|---|---|---|---|---|---|---|---|
| | | | $D_3$ | $D_4$ | $D_5$ | $D_6$ | $D_7$ | $D_8$ | $D_9$ $D_{10}$ |
| 1 | 15 min. | 78.7 | 0.4 | 93.8 | 3.0 | 0.4 | 0.1 | Tr | Tr Tr |
| 2 | 30 min. | 71.1 | 0.5 | 94.0 | 4.6 | 0.6 | 0.1 | — | — — |
| 3 | 1 hr. | 75.28 | 0.4 | 89.0 | 7.2 | 1.0 | 0.1 | 0.1 | Tr Tr |
| 4 | 2 hr. | 72.32 | 0.5 | 80.7 | 11.8 | 1.9 | 0.3 | 0.1 | 0.1 — |
| 5 | 3 hr. | 74 | 0.4 | 77.3 | 16.1 | 2.7 | 0.4 | 0.2 | 0.1 0.1 |
| 6 | 4 hr. | 73.7 | 0.4 | 72.4 | 19.8 | 3.4 | 0.6 | 0.2 | 0.1 0.1 |
| 7 | 6 hr. | 74 | 0.4 | 60.5 | 25.4 | 4.6 | 0.8 | 0.3 | 0.1 — |
| 8 | 8 hr. | 76.8 | 0.4 | 53.3 | 30.6 | 6.0 | 1.1 | 0.4 | — — |

| Summary of Raw Materials and Conditions Used in Example 1 | |
|---|---|
| $D_4$ | 60% |
| concentrated HCl | 39.4% |
| n-octylamine | 0.6% |
| temperature | 90° C. |
| pressure | atmospheric |
| agitation | moderate (500 rpm) |

EXAMPLE 2

The process described in Example 1 was repeated utilizing however 346.05 grams of concentrated HCl, 27.0 grams of n-octylamine and 526.95 grams of $D_4$. The $D_4$ used had the same analysis as the one used in Example 1. Samples were taken and treated in the same manner as described in Example 1. Table 2 below sets forth the time from time zero at which the sample was taken and the chromatographic analysis of cyclic polymers in each sample.

Comparing Table 2 with Table 1 it is clear that an increase of the weight % of n-octylamine from 0.6% to 3% reduces the length of time within which a substantial conversion to the cyclic pentamer occurs, e.g. a conversion to 31.9% took place in 15 minutes in Example 2 whereas in Example 1 an 8 hour reaction time was needed to produce 30.6% $D_5$.

TABLE 2

| Sample Number | Time From Time Zero | Sample Weight (Grams) | Chromatography Analysis (VPC), % | | | | | | |
|---|---|---|---|---|---|---|---|---|---|
| | | | $D_3$ | $D_4$ | $D_5$ | $D_6$ | $D_7$ | $D_8$ | $D_9$ $D_{10}$ |
| 1 | 15 min. | 75.4 | 1.5 | 44.3 | 31.9 | 8.8 | 2.0 | 0.7 | 0.4 0.3 |
| 2 | 30 min. | 75.3 | 0.4 | 32.8 | 30.7 | 11.6 | 3.1 | 1.3 | 0.7 0.5 |
| 3 | 1 hr. | 73.8 | 0.6 | 25.4 | 23.3 | 10.1 | 3.3 | 1.4 | 1.0 0.7 |
| 4 | 2 hr. | 70.1 | 0.2 | 18.9 | 16.0 | 6.8 | 2.3 | 1.0 | 0.8 0.7 |
| 5 | 3 hr. | 72.7 | 0.2 | 14.7 | 12.2 | 4.9 | 1.6 | 0.7 | 0.5 0.5 |
| 6 | 4 hr. | 73.5 | 0.3 | 13.1 | 10.2 | 3.9 | 1.2 | 0.5 | 0.4 0.4 |
| 7 | 6 hr. | 68.1 | 0.3 | 10.6 | 8.0 | 2.9 | 0.9 | 0.4 | 0.2 0.2 |
| 8 | 8 hr. | 67.5 | 0.1 | 9.7 | 7.1 | 2.6 | 0.8 | 0.3 | 0.2 0.1 |

| Summary of Raw Materials and Conditions Used in Example 2 | |
|---|---|
| $D_4$ | 58.55% |
| concentrated HCl | 38.45% |
| n-octylamine | 3.0% |
| temperature | 90° C. |
| pressure | atmospheric |
| agitation | moderate (500 rpm) |

EXAMPLE 3

The procedure of Example 1 was repeated using however 346.05 grams of concentrated HCl, 55.72 grams of n-octylamine and 526.95 grams of $D_4$. The $D_4$ used had the same analysis as that used in Example 1. Samples were taken after the time intervals from time zero given in Table 3, treated and analyzed as described in Example 1 with the following exceptions. Sample 1 was water washed at a 1:1 ratio with water two times and the bottom phase was drained off each time and the resulting top phase was then treated as described in Example 1. Samples 2 and 3 were treated the same as sample 1 except a 2:1 ratio of water to sample was used and only one wash with water was carried out. Samples 4 and 5 were first allowed to phase separate following withdrawal from the pot and the lower phase that formed was drained off and the upper phase was washed with an equal weight of water before neutralization, filtration and analysis of the top layer. The analytical results are given in Table 3 below.

The results illustrate that substantial yields of $D_5$ are obtained within 35 minutes when the n-octylamine concentration is increased even further to 6%.

TABLE 3

| Sample Number | Time From Time Zero | Sample Weight (Grams) | Chromatography Analysis (VPC), % | | | | | | |
|---|---|---|---|---|---|---|---|---|---|
| | | | $D_3$ | $D_4$ | $D_5$ | $D_6$ | $D_7$ | $D_8$ | $D_9$ $D_{10}$ |
| 1 | 15 min. | 74.8 | 0.1 | 57.7 | 17.4 | 6.4 | 1.8 | 0.7 | 0.4 0.3 |
| 2 | 35 min. | 77.1 | 0.1 | 20.4 | 18.1 | 7.7 | 2.6 | 1.2 | 0.8 0.7 |
| 3 | 1 hr. | 73.5 | 0.1 | 15.1 | 12.3 | 4.9 | 1.7 | 0.8 | 0.5 0.5 |
| 4 | 2 hr. | 74.8 | 0.1 | 11.3 | 8.5 | 3.3 | 1.0 | 0.4 | 0.3 0.3 |
| 5 | 3 hr. | 78.3 | 0.1 | 10.0 | 7.1 | 2.6 | 0.8 | 0.3 | 0.2 0.2 |
| 6 | 4 hr. | 77.3 | Tr | 9.3 | 6.6 | 2.4 | 0.7 | 0.3 | 0.2 0.1 |

| Summary of Raw Materials and Conditions Used in Example 3 | |
|---|---|
| $D_4$ | 56.74% |
| concentrated HCl | 37.26% |
| n-octylamine | 6% |
| temperature | 90° C. |
| pressure | atmospheric |
| agitation | moderate (500 rpm) |

EXAMPLE A (For Comparison Purposes)

The process described in Examples 2 and 3 was repeated utilizing however no n-octylamine and otherwise using no protonated amine. The $D_4$ starting material used in this example however was slightly different in that it contained 99.5% $D_4$, 0.12% $D_3$ and 0.29% $D_5$. Example A was conducted at a temperature of 90° C. as in Example 1 and at atmospheric pressure. A medium rate of agitation, e.g. 500 rpm, was used. Samples were taken and treated in the same manner as described in Example 1 and were also analyzed by vapor phase chromatography and the analytical results are given in Table 4 below.

Example A shows the maximum $D_5$ production was only 10.5% after 6 hours reaction time compared to 30.6% $D_5$ production in Example 1 after 8 hours, 31.9% $D_5$ production after 15 minutes in Example 2 and 18.1% $D_5$ production after 30 minutes in Example 3.

TABLE 4

| Sample Number | Time From Time Zero | Sample Weight (Grams) | Chromatography Analysis (VPC), % | | | | | | | |
|---|---|---|---|---|---|---|---|---|---|---|
| | | | $D_3$ | $D_4$ | $D_5$ | $D_6$ | $D_7$ | $D_8$ | $D_9$ | $D_{10}$ |
| 1 | 15 min | 66.9 | 0.3 | 98.3 | 0.9 | 0.1 | Tr | — | — | — |
| 2 | 30 min | 66.9 | 0.3 | 98.2 | 0.9 | 0.1 | Tr | — | — | — |
| 3 | 1 hr. | 70 | 0.3 | 98.0 | 1.4 | 0.2 | 0.1 | Tr | — | — |
| 4 | 2 hr. | 70.8 | 0.285 | 92.6 | 2.23 | 0.406 | 0.107 | 0.076 | 0.053 | 0.051 |
| 5 | 3 hr. | 71.4 | 0.3 | 86.6 | 3.0 | 0.5 | 0.1 | 0.1 | Tr | Tr |
| 6 | 4 hr. | 73.8 | 0.174 | 83.6 | 4.0 | 0.76 | 0.199 | 0.099 | 0.084 | 0.031 |
| 7 | 6 hr. | 80.2 | 0.121 | 41.6 | 10.2 | 2.3 | 0.7 | 0.261 | 0.162 | 0.099 |
| 8 | 8 hr. | 80.6 | 0.037 | 13.1 | 8.7 | 2.3 | 0.7 | 0.282 | 0.155 | 0.109 |

| Summary of Raw Materials and Conditions Used in Example A | |
|---|---|
| $D_4$ | 60.4% |
| concentrated HCl | 39.4% |
| n-octylamine | 0% |
| temperature | 90° C. |
| pressure | atmospheric |
| agitation | medium (500 rpm) |

EXAMPLE 4

The process described in Examples 2 and 3 was repeated. However, a slow agitation, e.g. 250 rpm, was used in place of the moderate agitation of Examples 1–3. The $D_4$ starting material used had the same analysis as that used in Example 1. Samples were taken of the product and they were treated in the same manner as described in Example 1. VPC analysis was conducted on each sample and the analytical results are given in Table 5 below.

This example and Examples 1–3 illustrate the advantages of using at least a moderate amount of agitation during the reaction in order to provide a significant amount of $D_5$ production.

TABLE 5

| Sample Number | Time From Time Zero | Sample Weight (Grams) | Chromatography Analysis (VPC), % | | | | | | | |
|---|---|---|---|---|---|---|---|---|---|---|
| | | | $D_3$ | $D_4$ | $D_5$ | $D_6$ | $D_7$ | $D_8$ | $D_9$ | $D_{10}$ |
| 1 | 15 min. | 83.0 | 0.3 | 98.7 | 0.1 | Tr | Tr | — | — | — |
| 2 | 30 min. | 78.5 | 0.3 | 98.7 | 0.9 | Tr | Tr | — | — | — |
| 3 | 1 hr. | 76.9 | 0.3 | 98.1 | 1.3 | 0.1 | Tr | Tr | Tr | Tr |
| 4 | 2 hr. | 80.9 | 0.4 | 97.8 | 1.6 | 0.2 | Tr | Tr | — | — |
| 5 | 3 hr. | 76.3 | 0.4 | 97.3 | 1.8 | 0.2 | 0.1 | Tr | — | — |
| 6 | 4 hr. | 71.9 | 0.4 | 97.2 | 1.9 | 0.3 | Tr | Tr | — | — |
| 7 | 6 hr. | 67.7 | 0.4 | 97.0 | 2.2 | 0.3 | Tr | Tr | Tr | Tr |
| 8 | 8 hr. | 68.7 | 0.4 | 96.5 | 2.6 | 0.4 | 0.1 | Tr | — | — |

| Summary of Raw Materials and Conditions Used in Example 4 | |
|---|---|
| $D_4$ | 60% |
| concentrated HCl | 39.4% |
| n-octylamine | 0.6% |
| temperature | 90° C. |
| pressure | atmospheric |
| agitation | slow (250 rpm) |

EXAMPLE 5

The process described in Example 4 was repeated however medium agitation (500 rpm) was used in place of the slow agitation of Example 4. The $D_4$ starting material used had the same analysis as that used in Example 1. Samples of the product were taken and were treated in the same manner as described in Example 1. VPC analysis was conducted on each sample and the analytical results are given in Table 6 below.

The results shown in Table 6 illustrate the excellent conversion of $D_4$ to $D_5$ over an 8 hour period.

TABLE 6

| Sample Number | Time From Time Zero | Sample Weight (Grams) | Chromatography Analysis (VPC), % | | | | | | | |
|---|---|---|---|---|---|---|---|---|---|---|
| | | | $D_3$ | $D_4$ | $D_5$ | $D_6$ | $D_7$ | $D_8$ | $D_9$ | $D_{10}$ |
| 1 | 15 min. | 75.1 | 0.4 | 94.9 | 4.0 | 0.5 | 0.1 | Tr | — | — |
| 2 | 30 min. | 73.0 | 0.4 | 92.4 | 6.2 | 0.8 | 0.1 | Tr | — | — |
| 3 | 1 hr. | 75.0 | 0.5 | 87.9 | 9.9 | 1.4 | 0.2 | 0.1 | Tr | Tr |
| 4 | 2 hr. | 76.3 | 0.4 | 80.6 | 15.9 | 2.4 | 0.4 | 0.1 | Tr | — |
| 5 | 3 hr. | 75.1 | 0.3 | 72.1 | 20.4 | 3.2 | 0.5 | 0.2 | 0.1 | — |
| 6 | 4 hr. | 74.9 | 0.3 | 66.0 | 24.9 | 4.1 | 0.7 | 0.2 | 0.1 | 0.1 |
| 7 | 6 hr. | 73.3 | 0.3 | 56.5 | 30.6 | 5.5 | 0.9 | 0.3 | 0.1 | Tr |
| 8 | 8 hr. | 76.3 | 0.3 | 50.0 | 33.7 | 6.6 | 1.1 | 0.4 | 0.2 | 0.1 |

| Summary of Raw Materials and Conditions Used in Example 5 | |
|---|---|
| $D_4$ | 60% |
| concentrated HCl | 39.4% |
| n-octylamine | 0.6% |
| temperature | 90° C. |
| pressure | atmospheric |
| agitation | medium (500 rpm) |

EXAMPLE 6

The process described in Example 4 was repeated. However, a rapid agitation, e.g. 850 rpm, was used in place of the slow agitation of Example 4. The $D_4$ starting material used had the same analysis as that used in Example 1. Samples of the product were taken and they were treated in the same manner as described in Example 1. VPC analysis was conducted on each sample and the analytical results are given in Table 7 below.

This example shows the sharp increase in $D_5$ production by increasing the speed of agitation.

TABLE 7

| Sample Number | Time From Time Zero | Sample Weight (Grams) | Chromatography Analysis (VPC), % | | | | | | | |
|---|---|---|---|---|---|---|---|---|---|---|
| | | | $D_3$ | $D_4$ | $D_5$ | $D_6$ | $D_7$ | $D_8$ | $D_9$ | $D_{10}$ |
| 1 | 15 min. | 72.6 | 0.5 | 92.2 | 6.3 | 0.8 | 0.1 | Tr | Tr | Tr |
| 2 | 30 min. | 73.8 | 0.5 | 86.8 | 10.8 | 1.4 | 0.2 | 0.1 | 0.1 | 0.1 |

TABLE 7-continued

| Sample Number | Time From Time Zero | Sample Weight (Grams) | Chromatography Analysis (VPC), % | | | | | | | |
|---|---|---|---|---|---|---|---|---|---|---|
| | | | $D_3$ | $D_4$ | $D_5$ | $D_6$ | $D_7$ | $D_8$ | $D_9$ | $D_{10}$ |
| 3 | 1 hr. | 72.7 | 0.4 | 78.5 | 17.6 | 2.4 | 0.4 | 0.1 | 0.1 | Tr |
| 4 | 2 hr 6 min | 71.2 | 0.8 | 64.6 | 27.8 | 4.3 | 0.7 | 0.3 | 0.2 | Tr |
| 5 | 3 hr. | 72 | 0.3 | 56.4 | 33.2 | 5.6 | 1.0 | 0.3 | 0.2 | Tr |
| 6 | 4 hr 7 min | 72.6 | 0.3 | 45.5 | 33.5 | 6.3 | 1.2 | 0.4 | 0.2 | 0.1 |
| 7 | 6 hr. | 74.7 | 0.3 | 39.7 | 35.1 | 7.8 | 1.5 | 0.5 | 0.3 | 0.2 |
| 8 | 8 hr. | 75.9 | 0.2 | 34.5 | 33.0 | 8.5 | 1.7 | 0.6 | 0.3 | 0.2 |

| Summary of Raw Materials and Conditions Used in Example 6 | |
|---|---|
| $D_4$ | 60% |
| concentrated HCl | 39.4% |
| n-octylamine | 0.6% |
| temperature | 90° C. |
| pressure | atmospheric |
| agitation | moderate (850 rpm) |

EXAMPLE 7

The process of Example 1 was carried out using the same type of $D_4$ described in Example 1 but however using 526.95 g (59.64%) $D_4$, 364.05 g. (39.16%) concentrated hydrochloric acid, 10.6 g. (1.2%) n-octylamine and fast agitation (850 rpm). Samples were taken after the time intervals indicated in Table 8 below, they were treated as described in Example 1 and vapor phase chromatographic analyses were performed on them. The results are given in Table 8.

A comparison of the results shown in Table 8 with the results shown in Tables 1 and 6 illustrates the advantageous effects of fast agitation and moderately increased amounts of n-octylamine in lowering the time to produce maximum yield of $D_5$ from 8 hours or more in Table 1 or 6 hours in Table 6 down to 1 hour as shown by this example.

TABLE 8

| Sample Number | Time From Time Zero | Sample Weight (Grams) | Chromatography Analysis (VPC), % | | | | | | | |
|---|---|---|---|---|---|---|---|---|---|---|
| | | | $D_3$ | $D_4$ | $D_5$ | $D_6$ | $D_7$ | $D_8$ | $D_9$ | $D_{10}$ |
| 1 | 15 min. | 74.5 | 0.4 | 70.1 | 23.6 | 4.3 | 0.8 | 0.2 | 0.1 | 0.1 |
| 2 | 30 min. | 74.3 | 0.3 | 56.5 | 33.2 | 6.9 | 1.3 | 0.5 | 0.3 | 0.2 |
| 3 | 1 hr. | 74.7 | 0.2 | 39.1 | 33.4 | 8.8 | 1.8 | 0.6 | 0.3 | 0.2 |
| 4 | 2 hr. | 76.1 | 0.2 | 34.8 | 33.0 | 11.9 | 3.0 | 1.1 | 0.5 | 0.3 |
| 5 | 3 hr. | 73 | 0.1 | 29.0 | 27.3 | 11.2 | 3.1 | 1.2 | 0.6 | 0.6 |
| 6 | 4 hr 6 min | 74.3 | 0.1 | 25.8 | 23.7 | 10.4 | 3.2 | 1.2 | 0.8 | 0.5 |
| 7 | 6 hr. | 74.3 | 0.1 | 23.3 | 20.3 | 9.2 | 3.1 | 1.3 | 0.9 | 0.6 |
| 8 | 8 hr. | 73.9 | 0.1 | 19.8 | 17.3 | 7.5 | 2.6 | 1.1 | 0.8 | 0.6 |

| Summary of Raw Materials and Conditions Used for Example 7 | |
|---|---|
| $D_4$ | 59.64% |
| concentrated HCl | 39.16% |
| n-octylamine | 1.2% |
| temperature | 90° C. |
| pressure | atmospheric |
| agitation | fast (850 rpm) |

EXAMPLE 8

The process as described in Example 4 was used wherein however a 20 wt. % aqueous HCl solution was substituted for the aqueous concentrated HCl solution. Thus, 39.4% of the 20% aqueous HCl solution, 0.6% n-octylamine and 60% of $D_4$ was used. The $D_4$ starting material used in this example had the same analysis as the one described in Example A. A medium rate of agitation (500 rpm) was used instead of the slow agitation (250 rpm) used in Example 4. Samples were taken of the product and they were treated in the same manner as described in Example 1. VPC analysis was conducted on each sample and the analytical results are given in Table 9 below.

Comparing this example with Examples 1–7, it is shown that a more dilute aqueous hydrochloric acid solution results in a longer reaction time and a lower conversion from $D_4$ to $D_5$ than in those cases where an aqueous concentrated hydrochloric acid solution was used. Comparing the results of this example with those of Example A, it is clear nevertheless that substantially better converstions of $D_4$ to $D_5$ are obtained in the presence of even small amounts of n-octylamine in spite of the use of the more dilute aqueous hydrochloric acid solution.

TABLE 9

| Sample Number | Time From Time Zero | Sample Weight (Grams) | Chromatography Analysis (VPC), % | | | | | | | |
|---|---|---|---|---|---|---|---|---|---|---|
| | | | $D_3$ | $D_4$ | $D_5$ | $D_6$ | $D_7$ | $D_8$ | $D_9$ | $D_{10}$ |
| 1 | 15 min | 70.1 | 0.596 | 97.85 | 1.276 | 0.118 | — | — | — | — |
| 2 | 30 min | 70.6 | 0.6 | 94.0 | 1.8 | 0.1 | — | — | — | — |
| 3 | 1 hr. | 71.5 | 0.6 | 95.0 | 3.3 | 0.3 | 0.1 | — | — | — |
| 4 | 2 hr. | 72.1 | 0.7 | 92.4 | 5.9 | 0.6 | 0.1 | Tr | Tr | — |
| 5 | 3 hr. | 74.4 | 0.611 | 88.27 | 8.167 | 0.819 | 0.129 | 0.037 | Tr | — |
| 6 | 4 hr. | 74.2 | 0.585 | 84.83 | 10.47 | 1.053 | 0.142 | 0.047 | — | 0.083 |
| 7 | 6 hr. | 69.8 | 0.6 | 82.0 | 14.9 | 1.6 | 0.3 | 0.1 | Tr | Tr |
| 8 | 8 hr. | 71.4 | 0.5 | 74.0 | 17.6 | 2.0 | 0.3 | 0.2 | 0.1 | 0.1 |

| Summary Of Raw Materials and Conditions Used in Example 8 | |
|---|---|
| $D_4$ | 60% |
| 20 wt. % aqueous HCl | 39.4% |
| n-octylamine | 0.6% |
| temperature | 90° C. |
| pressure | atmospheric |
| agitation | medium (500 rpm) |

EXAMPLE 9

The process as described in Example 8 was carried out wherein however 10.6 g. of n-octylamine was used in place of the 5.27 g. of n-octylamine used in Example 8. Samples were taken of the product at the time intervals specified in Table 10 below, the samples were treated in the same manner as described in Example 1 and VPC analysis was performed on each sample. The analytical results are given in Table 10 below. Comparing these results with those of Example 8, it is clearly seen that by doubling the n-octylamine amount the rate of conversion from $D_4$ to $D_5$ reached 17.2% $D_5$ within 1 hour and exceeded 33% $D_5$ in 6 hours whereas in Example 8 it took 8 hours to achieve a 17.6% $D_5$ conversion.

TABLE 10

| Sample Number | Time From Time Zero | Sample Weight (Grams) | $D_3$ | $D_4$ | $D_5$ | $D_6$ | $D_7$ | $D_8$ | $D_9$ | $D_{10}$ |
|---|---|---|---|---|---|---|---|---|---|---|
| 1 | 15 min. | 72.4 | 0.5 | 91.6 | 6.4 | 0.9 | 0.2 | Tr | Tr | Tr |
| 2 | 30 min. | 73.3 | 0.6 | 85.3 | 11.0 | 1.6 | 0.3 | 0.1 | — | — |
| 3 | 1 hr. | 73.6 | 0.5 | 71.7 | 17.2 | 2.7 | 0.5 | 0.2 | 0.1 | Tr |
| 4 | 2 hr. | 72.9 | 0.4 | 59.0 | 26.4 | 4.5 | 0.8 | 0.3 | 0.2 | 0.1 |
| 5 | 3 hr. | 74.5 | 0.4 | 49.4 | 30.7 | 5.9 | 1.1 | 0.4 | 0.2 | 0.1 |
| 6 | 4 hr. | 74.0 | 0.3 | 43.9 | 33.6 | 4.4 | 1.4 | 0.5 | 0.3 | 0.2 |
| 7 | 6 hr. | 72.2 | 0.3 | 36.2 | 33.0 | 9.0 | 1.9 | 0.7 | 0.4 | 0.3 |
| 8 | 8 hr. | 72.9 | 0.3 | 32.7 | 36.4 | 10.0 | 2.2 | 0.8 | 0.4 | 0.3 |

| Summary of Raw Materials and Conditions Used in Example 9 | |
|---|---|
| $D_4$ | 59.61% |
| 20 wt. % aqueous HCl | 39.16% |
| n-octylamine | 1.2% |
| temperature | 90° C. |
| pressure | atmospheric |
| agitation | medium (500 rpm) |

EXAMPLE 10

In this example, 383.81 g. (40.1%) of concentrated HCl and 5.77 g. (0.6%) of n-octylamine were charged to a 1000 ml bottom takeoff pot equipped as described in Example 1. Stirring was begun and the contents of the pot were heated to 90° C. for about 35 minutes at which time it was lined out at about 90° C. Over a period of 10 minutes 568.04 g. (59.3%) of $D_4$ was added to the pot at a steady rate. During addition the temperature dropped to 80° C. and was lined back out at 90° C. within about 6 minutes. Time zero was counted from the time (9;22 a.m.) at which about half the $D_4$ charge had been added. At the time intervals from time zero as listed in Table 11 below, samples were taken through the bottom takeoff and were treated in the manner described in Example 1, following which each sample was analyzed by VPC. The analytical results are given in Table 11 below.

TABLE 11

| Sample Number | Time From Time Zero | $D_3$ | $D_4$ | $D_5$ | $D_6$ | $D_7$ | $D_8$ | $D_9$ | $D_{10}$ |
|---|---|---|---|---|---|---|---|---|---|
| 1 | 15 min. | 0.4 | 94.1 | 3.1 | 0.4 | — | — | — | — |
| 2 | 30 min. | 0.4 | 90.4 | 5.6 | 0.8 | — | — | — | — |
| 3 | 1 hr. | 0.3 | 84 | 9.8 | 1.4 | 0.2 | Tr | — | — |
| 4 | 2 hr. | 0.3 | 73.4 | 16.0 | 3.0 | 0.4 | 0.1 | Tr | Tr |
| 5 | 3 hr. | 0.3 | 58.9 | 27.8 | 5.1 | 0.8 | 0.2 | — | — |

| Summary of Raw Materials and Conditions Used in Example 9 | |
|---|---|
| $D_4$ | 59.3% |
| concentrated HCl | 40.1% |
| n-octylamine | 0.6% |
| temperature | 90° C. |
| pressure | atmospheric |
| agitation | moderate |

EXAMPLE B

The apparatus described in Example 1 was used in this example. 177.3 g. of concentrated HCl was added to the pot and agitation at 500 rpm was begun. 2.7 g. of n-octylamine was added to the pot and the pot contents were heated to 90° C. A mixture of 270 g. of $D_4$ in 450 g. toluene was added to the pot. Time zero was recorded as that time in which one-half the $D_4$/toluene mixture had been added and the pot was lined out at 90° C. The $D_4$ used in this example had the same analysis as that used in Example A. Samples were removed after the time intervals given in Table 12 and treated as described in Example 1 and analyzed by VPC. The analytical results are presented in Table 12 below.

As can be observed in Table 12, toluene operated to reduce the amount of $D_4$ converted to $D_5$.

TABLE 12

| Sample Number | Time From Time Zero | Sample Weight Grams | Toluene | $D_3$ | $D_4$ | $D_5$ | $D_6$ | $D_7$ | $D_8$ | $D_9$ | $D_{10}$ |
|---|---|---|---|---|---|---|---|---|---|---|---|
| 1 | 15 min | 66.7 | 69.1 | 0.6 | 29.4 | 0.7 | 0.1 | Tr | — | — | — |
| 2 | 30 min | 67.1 | 68.9 | 0.6 | 29.1 | 1.0 | 0.1 | Tr | — | — | — |
| 3 | 1 hr. | 66.4 | 69.1 | 0.6 | 28.6 | 1.4 | 0.1 | Tr | — | — | — |
| 4 | 2 hr. | 68.6 | 68.95 | 0.489 | 27.840 | 2.135 | 0.217 | 0.040 | 0.010 | 0.004 | |
| 5 | 3 hr. | 68.7 | 69.22 | 0.598 | 26.866 | 2.810 | 0.293 | 0.048 | 0.035 | — | — |
| 6 | 4 hr. | 68.3 | 69.1 | 0.6 | 26.3 | 3.4 | 0.4 | 0.1 | Tr | Tr | Tr |
| 7 | 6 hr. | 67 | 69.138 | 0.631 | 24.939 | 4.513 | 0.506 | 0.088 | 0.047 | 0.031 | 0.008 |
| 8 | 8 hr. | 68.8 | 69.195 | 0.576 | 23.916 | 5.381 | 0.641 | 0.105 | 0.051 | 0.014 | 0.017 |

| Summary of Raw Materials and Conditions Used in Example B | |
|---|---|
| $D_4$ | 30% |
| concentrated HCl | 19.7% |
| n-octylamine | 0.3% |
| toluene | 50% |
| temperature | 90° C. |
| pressure | atmospheric |
| agitation | moderate |

EXAMPLE C

The procedure described for Example 4 was repeated in this example except that a moderate agitation (500 rpm) was used instead of a slow agitation (250 rpm) and tetradecanol was used in place of n-octylamine. Samples were withdrawn at the time intervals given in Table 13, treated as described in Example 1 and analyzed by VPC analysis. The $D_4$ used had the same analysis as that used in Examples A and B. The results are given in Table 13 below.

As seen from the results in Table 13 and comparing same with the results of Table 4, there appears to be no improvement in the conversion yield of $D_5$ to $D_4$.

TABLE 13

| Sample Number | Time From Time Zero | Sample Weight (Grams) | Chromatography Analysis (VPC), % | | | | | | | |
|---|---|---|---|---|---|---|---|---|---|---|
| | | | $D_3$ | $D_4$ | $D_5$ | $D_6$ | $D_7$ | $D_8$ | $D_9$ | $D_{10}$ |
| 1 | 15 min | 70.2 | 0.3 | 90.0 | 0.5 | Tr | Tr | 0.9 | — | — |
| 2 | 30 min | 67.1 | 0.4 | 90.5 | 0.9 | 0.1 | 0.1 | 0.9 | Tr | Tr |
| 3 | 1 hr. | 69.6 | 0.5 | 97.1 | 0.9 | 0.1 | Tr | 0.9 | — | — |
| 4 | 2 hr. | 69.3 | 0.487 | 93.854 | 1.389 | 0.225 | 0.079 | 0.717 | 0.038 | 0.013 |
| 5 | 3 hr. | 69.9 | 0.454 | 93.142 | 1.929 | 0.340 | 0.147 | 0.703 | 0.023 | 0.015 |
| 6 | 4 hr. | 69.1 | 0.451 | 90.754 | 2.682 | 0.500 | 0.145 | 0.584 | 0.033 | 0.045 |
| 7 | 6 hr. | 73.7 | 0.382 | 83.256 | 4.258 | 0.850 | 0.250 | 0.483 | 0.063 | 0.044 |
| 8 | 8 hr. | 76.4 | 0.324 | 77.169 | 6.991 | 1.457 | 0.416 | 0.397 | 0.095 | 0.067 |

| Summary of Raw Materials and Conditions Used in Example C | |
|---|---|
| $D_4$ | 60% |
| concentrated HCl | 39.4% |
| tetradecanol | 0.6% |
| temperature | 90° C. |
| pressure | atmospheric |
| agitation | medium (500 rpm) |

EXAMPLE D

The procedure described for Example 4 was repeated in this example except that a moderate agitation (500 rpm) was used instead of a slow agitation (250 rpm) and n-butylamine was used in place of n-octylamine. Samples were withdrawn at the time intervals given in Table 14, treated as described in Example 1 and analyzed by VPC analysis. The $D_4$ used had the same analysis as that used in Examples A and B. The results are given in Table 14 below.

TABLE 14

| Sample Number | Time From Time Zero | Sample Weight (Grams) | Chromatography Analysis (VPC), % | | | | | | | |
|---|---|---|---|---|---|---|---|---|---|---|
| | | | $D_3$ | $D_4$ | $D_5$ | $D_6$ | $D_7$ | $D_8$ | $D_9$ | $D_{10}$ |
| 1 | 15 min | 68 | 0.2 | 95.8 | 0.4 | Tr | Tr | — | — | — |
| 2 | 30 min | 69.9 | 0.3 | 98.5 | 0.6 | 0.1 | 0.1 | Tr | Tr | Tr |
| 3 | 1 hr. | 71.5 | 0.4 | 98.1 | 0.9 | 0.1 | 0.1 | Tr | — | — |
| 4 | 2 hr. | 70.8 | 0.395 | 92.510 | 1.437 | 0.247 | 0.069 | 0.034 | 0.024 | 0.034 |
| 5 | 3 hr. | 71.2 | 0.342 | 91.248 | 2.002 | 0.351 | 0.117 | 0.043 | 0.034 | 0.017 |
| 6 | 4 hr. | 72.1 | 0.350 | 87.825 | 2.583 | 0.470 | 0.128 | 0.069 | 0.032 | 0.029 |
| 7 | 6 hr. | 72.5 | 0.317 | 83.759 | 4.048 | 0.762 | 0.212 | 0.081 | 0.055 | 0.037 |
| 8 | 8 hr. | 74.9 | 0.210 | 78.205 | 5.591 | 1.102 | 0.317 | 0.148 | 0.091 | 0.052 |

| Summary of Raw Materials and Conditions Used in Example D | |
|---|---|
| $D_4$ | 60% |
| concentrated HCl | 39.4% |
| n-butylamine | 0.6% |
| temperature | 90° C. |
| pressure | atmospheric |
| agitation | medium (500 rpm) |

EXAMPLE E

Into a 1000 ml, three-neck, bottom takeoff pot equipped with a mechanical agitator, an addition funnel, a Friedrich water condenser, thermometer, and heating mantel fitted with a pot watcher, there were charged 758.3 g. of $D_4$ having an analysis similar to that given for the $D_4$ in Example A. There was then added to the addition funnel 5.27 g. of Arquad T-50, a cationic quaternary ammonium salt of the alkyl trimethyl ammonium chloride and dialkyldiethyl ammonium chloride types in which the alkyl chains range from 8 to 18 carbon atoms. Agitation was begun at 500 rpm and the pot was heated up to 90° C. which was designated as time zero. An additional 114.7 g. $D_4$ was added through the addition funnel into the pot. At 15 minutes from time zero and at various other time intervals from time zero as given in Table 15, samples were removed, washed with water, neutralized with sodium bicarbonate, filtered and analyzed by VPC. The analytical results are given in Table 15. In this example no aqueous hydrochloric acid solution was used. The results show substantially no conversion from $D_4$ to $D_5$.

TABLE 15

| Sample Number | Time From Time Zero | Sample Weight (Grams) | Chromatography Analysis (VPC), % | | | | | | | |
|---|---|---|---|---|---|---|---|---|---|---|
| | | | $D_3$ | $D_4$ | $D_5$ | $D_6$ | $D_7$ | $D_8$ | $D_9$ | $D_{10}$ |
| 1 | 15 min. | 66.7 | 0.1 | 99.4 | 0.3 | — | — | — | — | — |
| 2 | 30 min. | 67.7 | 0.124 | 99.430 | 0.278 | 0.011 | — | — | — | — |
| 3 | 1 hr. | 65.5 | 0.158 | 99.196 | 0.298 | 0.007 | — | — | — | — |
| 4 | 2 hr. | 64 | 0.176 | 99.222 | 0.275 | — | — | — | — | — |

TABLE 15-continued

| Sample Number | Time From Time Zero | Sample Weight (Grams) | Chromatography Analysis (VPC), % | | | | | | |
|---|---|---|---|---|---|---|---|---|---|
| | | | $D_3$ | $D_4$ | $D_5$ | $D_6$ | $D_7$ | $D_8$ | $D_9$ $D_{10}$ |
| 5 | 3 hr. | 68.2 | 0.160 | 99.281 | 0.281 | — | 0.014 | — | — — |
| 6 | 4 hr. | 66.1 | 0.1 | 96.1 | 0.3 | — | — | — | — — |
| 7 | 6 hr. | 67.6 | 0.1 | 98.9 | 0.3 | — | — | — | — — |
| 8 | 8 hr. | 70.3 | 0.1 | 99.2 | 0.3 | — | — | — | — — |

| Summary of Raw Materials and Conditions used in Example E | |
|---|---|
| $D_4$ | 99.4% |
| concentrated HCl | 0 |
| n-octylamine | 0 |
| quaternary ammonium chloride | 0.6% |
| temperature | 90° C. |
| pressure | atmospheric |
| agitation | moderate (500 rpm) |

EXAMPLE F

This example demonstrates that the process of this invention is capable of producing small amounts of $D_6$ from $D_5$ when $D_5$ is used in the process in place of $D_4$. In this example the procedure described for Example 4 was repeated except that a moderate agitation (500 rpm) was used instead of a slow agitation (250 rpm) and $D_5$ was substituted weight-by-weight for the $D_4$ used for Example 4. The $D_5$ starting material used contained 96.873% $D_5$, 0.788% $D_4$, 0.022% $D_3$, 1.069% $D_6$ and 0.019% $D_7$. Samples were withdrawn at the time intervals given in Table 16, treated as described in Example 1 and analyzed by VPC analysis. The results are given in Table 16 below.

TABLE 16

| Sample Number | Time From Time Zero | Sample Weight (Grams) | Chromatography Analysis (VPC), % | | | | | | |
|---|---|---|---|---|---|---|---|---|---|
| | | | $D_3$ | $D_4$ | $D_5$ | $D_6$ | $D_7$ | $D_8$ | $D_9$ $D_{10}$ |
| 1 | 15 min. | 74.8 | 0.192 | 4.013 | 93.376 | 1.176 | 0.054 | — | Tr — |
| 2 | 30 min. | 75.3 | 0.193 | 6.266 | 90.857 | 1.305 | 0.043 | 0.004 | Tr — |
| 3 | 1 hr. | 73.1 | 0.243 | 10.33 | 86.474 | 1.461 | 0.044 | 0.044 | — Tr |
| 4 | 2 hr. | 75.8 | 0.270 | 17.39 | 78.814 | 1.859 | 0.074 | 0.084 | 0.047 Tr |
| 5 | 3 hr. | 75.3 | 0.274 | 23.081 | 72.528 | 2.349 | 0.046 | 0.129 | 0.041 Tr |
| 6 | 4 hr. | 74.5 | 0.299 | 27.765 | 67.214 | 2.859 | 0.055 | 0.139 | 0.047 Tr |
| 7 | 6 hr. | 75.4 | 0.323 | 32.429 | 55.633 | 3.831 | 0.520 | 0.221 | 0.095 Tr |
| 8 | 8 hr. | 73.6 | 0.302 | 35.476 | 51.066 | 4.821 | 0.720 | 0.256 | 0.117 0.080 |

| Summary of Raw Materials and Conditions Used in Example F | |
|---|---|
| $D_5$ | 60% |
| concentrated HCl | 39.45% |
| n-octylamine | 0.6% |
| temperature | 90° C. |
| pressure | atmospheric |
| agitation | moderate (500 rpm) |

EXAMPLE G

The procedure described in Examples C and D was repeated in this example except that Arquad T-50 (which is described in Example F) was substituted on a weight-for-weight basis for tetradecanol. Samples were withdrawn at the time intervals given in Table 17, treated as described in Example 1 and analyzed by VPC analysis. The $D_4$ starting material had the same analysis as the $D_4$ starting materials described in Example C. This example shows a very low conversion of $D_4$ to $D_5$ even after an extended period of 4 hours.

TABLE 17

| Sample Number | Time From Time Zero | Sample Weight (Grams) | Chromatography Analysis (VPC), % | | | | | | |
|---|---|---|---|---|---|---|---|---|---|
| | | | $D_3$ | $D_4$ | $D_5$ | $D_6$ | $D_7$ | $D_8$ | $D_9$ $D_{10}$ |
| 1 | 15 min. | 73.2 | 0.247 | 98.29 | 0.849 | 0.078 | 0.018 | 0.017 | — 0.008 |
| 2 | 30 min. | 70.3 | 0.230 | 98.13 | 0.969 | 0.118 | 0.059 | 0.011 | — 0.012 |
| 3 | 1 hr. | 73.8 | 0.242 | 97.73 | 1.269 | 0.162 | 0.037 | 0.012 | — 0.011 |
| 4 | 2 hr. | 75.3 | 0.241 | 96.78 | 1.902 | 0.304 | 0.084 | 0.016 | 0.006 0.016 |
| 5 | 3 hr. | 75.2 | 0.180 | 77.89 | 2.737 | 0.480 | 0.118 | 0.053 | 0.023 0.022 |
| 6 | 4 hr. | 72.7 | 0.137 | 55.058 | 5.165 | 1.038 | 0.265 | 0.113 | 0.070 0.029 |

| Summary of Raw Materials and Conditions Used in Example G | |
|---|---|
| $D_4$ | 60% |
| concentrated HCl | 39.4% |
| Arquad T-50 | 0.6% |
| temperature | 90° C. |
| pressure | atmospheric |
| agitation | medium (500 rpm) |

EXAMPLE H

The procedure described for Example C was repeated in this example except that dibutyl ether was used weight for weight in place of tetradecanol. Samples were withdrawn at the time intervals given in Table 18, treated as described in Example 1 and analyzed by VPC analysis. The $D_4$ used had the same analysis as that used in Example C. The analytical results are given in Table 18. This example shows that very small amounts of $D_5$ were produced after a long reaction period.

TABLE 18

| Sample Number | Time From Time Zero | Sample Weight (Grams) | Chromatography Analysis (VPC), % | | | | | | | |
|---|---|---|---|---|---|---|---|---|---|---|
| | | | $D_3$ | $D_4$ | $D_5$ | $D_6$ | $D_7$ | $D_8$ | $D_9$ | $D_{10}$ |
| 1 | 15 min. | 68.7 | 0.248 | 95.269 | 0.405 | 0.059 | 0.021 | — | 0.011 | — |
| 2 | 30 min. | 67.9 | 0.320 | 96.939 | 0.541 | 0.087 | 0.026 | 0.020 | 0.007 | 0.026 |
| 3 | 1 hr. | 68.2 | 0.377 | 94.033 | 0.789 | 0.121 | 0.044 | 0.029 | 0.033 | 0.021 |
| 4 | 2 hr. | 65.7 | 0.320 | 89.854 | 1.303 | 0.229 | 0.059 | 0.033 | 0.029 | 0.018 |
| 5 | 3 hr. | 69.4 | 0.341 | 92.307 | 2.004 | 0.351 | 0.103 | 0.058 | 0.024 | 0.024 |
| 6 | 4 hr. | 66.7 | 0.348 | 88.403 | 2.619 | 0.485 | 0.138 | 0.057 | 0.028 | 0.020 |
| 7 | 6 hr. | 70.6 | 0.373 | 82.385 | 4.174 | 0.791 | 0.224 | 0.103 | 0.049 | 0.038 |
| 8 | 8 hr. | 79.5 | 0.282 | 70.117 | 6.693 | 1.345 | 0.356 | 0.008 | 0.068 | 0.052 |

| Summary of Raw Materials and Conditions Used in Example H | |
|---|---|
| $D_4$ | 60% |
| concentrated HCl | 39.4% |
| dibutyl ether | 0.6% |
| temperature | 90° C. |
| pressure | atmospheric |
| agitation | medium (500 rpm) |

EXAMPLE I

The procedure described for Example C was carried out wherein however Fluorad FC-95, a fluoro chemical surfactant made and sold by 3-M Company, was used in place of the tetradecanol used in Example C. Samples were withdrawn at the time intervals given in Table 19, treated as described in Example 1 and analyzed by VPC analysis. The $D_4$ used had the same analysis as the $D_4$ used in Example C. This example illustrates the production of very low amounts of $D_5$ even after 2 hours of reaction which compares very poorly with the production of $D_5$ from $D_4$ obtained by those examples of this invention in which moderate (medium) or fast agitation was used, e.g., Examples 1–3 and 5–8.

TABLE 19

| Sample Number | Time From Time Zero | Sample Weight (Grams) | Chromatography Analysis (VPC), % | | | | | | | |
|---|---|---|---|---|---|---|---|---|---|---|
| | | | $D_3$ | $D_4$ | $D_5$ | $D_6$ | $D_7$ | $D_8$ | $D_9$ | $D_{10}$ |
| 1 | 15 min. | 73.5 | 0.088 | 95.406 | 2.426 | 0.630 | 0.364 | 0.267 | 0.101 | 0.100 |
| 2 | 30 min. | 74 | 0.101 | 92.714 | 4.104 | 0.999 | 0.655 | 0.416 | 0.188 | 0.112 |
| 3 | 1 hr. | 72.5 | 0.095 | 88.798 | 6.655 | 1.644 | 1.0 | 0.542 | 0.224 | 0.166 |
| 4 | 2 hr. | 74.9 | — | 36.8 | 10.1 | 2.7 | 1.1 | 0.3 | — | — |

| Summary of Raw Materials and Conditions Used in Example I | |
|---|---|
| $D_4$ | 60% |
| concentrated HCl | 39.4% |
| Fluorad FC-95 | 0.6% |
| temperature | 90° C. |
| pressure | atmospheric |
| agitation | moderate |

What is claimed is:

1. A process for preparing decamethylcyclopentasiloxane from octamethylcyclotetrasiloxane by heating the latter with aqueous hydrochloric acid and a salt of a protonated amine having at least one nitrogen-bonded monovalent hydrocarbon group having 5 to 14 carbon atoms at a temperature in excess of 60° C.

2. Process as claimed in claim 1 wherein said protonated amine salt has the formula: RR'R"N+H.X− wherein R is a monovalent hydrocarbon group having 5 to 14 carbon atoms, R' and R" are each a hydrogen atom or a monovalent hydrocarbon group having 1 to 4 carbon atoms, and X is a mineral acid anion.

3. Process as claimed in claim 2 wherein said protonated amine salt has the formula: RR'R"N+H.X− wherein R is an alkyl group having 5 to 14 carbon atoms, R' and R" are each a hydrogen atom or an alkyl group having 1 to 4 carbon atoms, and X is a mineral acid anion.

4. Process as claimed in claim 1 wherein said protonated amine salt is formed in situ by adding an amine having at least one nitrogen-bonded monovalent hydrocarbon group having 5 to 14 carbon atoms to said aqueous hydrochloric acid.

5. Process as claimed in claim 1 wherein the concentration of said protonated amine salt is in the range of 0.1 to 10 wt. % of the total weight of aqueous hydrochloric acid, octamethylcyclotetrasiloxane and said protonated amine salt used in the process.

6. Process as claimed in claim 5 wherein the concentration of said protonated amine salt is in the range of 0.5 to 5 wt. % based on the same weight basis given in claim 5.

7. Process as claimed in claim 1 wherein said temperature is in the range of 60° to 180° C.

8. Process as claimed in claim 1 wherein the pressure under which the process is carried out ranges from 1 to 50 atmospheres.

9. Process as claimed in claim 1 wherein the weight ratio of hydrogen chloride to water in the aqueous hydrochloric acid is at least 0.25.

10. Process as claimed in claim 1 wherein the weight ratio of octamethylcyclotetrasiloxane to hydrochloric acid is less than 9.

11. Process as claimed in claim 10 wherein said weight ratio ranges from 0.3 to 5.

12. Process as claimed in claim 1 wherein the product produced by heating the octamethylcyclotetrasiloxane, aqueous hydrochloric acid and said protonated amine salt is neutralized by contacting it with water.

13. Process as claimed in claim 12 wherein the temperature of the neutralizing water is above 50° C.

14. In a process involving the hydrolysis and condensation of dimethyldichlorosilane to produce an acid cyclic hydrolyzate, neutralizing and water washing said hydrolyzate to provide a mixture of linear and cyclic polysiloxanes and recovering and separating said cyclic siloxanes into fractions including octamethylcyclotetrasiloxane and decamethylcyclopentasiloxane, the improvement of increasing the yield of decamethylcyclopentasiloxane, comprising treating said octamethylcyclotetrasiloxane fraction by the process claimed in claim 1 to convert octamethylcyclotetrasiloxane to decamethylcyclopentasiloxane, allowing the resulting mixture to phase separate into a silicone phase containing said decamethylcyclopentasiloxane and an aqueous phase containing said aqueous hydrochloric acid and said protonated amine salt, recycling said aqueous phase for mixing with additional octamethylcyclotetrasiloxane provided by said fractionation step and mixing said silicone phase with said acid cyclic hydrolyzate and proceeding with said neutralization and water wash steps to provide said mixture of linear and cyclic polysiloxanes.

* * * * *